(12) United States Patent
Ono

(10) Patent No.: US 7,338,584 B2
(45) Date of Patent: Mar. 4, 2008

(54) ELECTROPHORESIS APPARATUS

(75) Inventor: Koichi Ono, Kawaguchi (JP)

(73) Assignee: Enplas Corporation, Saitama (JP)

( * ) Notice: Subject to any disclaimer, the term of this patent is extended or adjusted under 35 U.S.C. 154(b) by 306 days.

(21) Appl. No.: 11/167,453

(22) Filed: Jun. 27, 2005

(65) Prior Publication Data

US 2005/0284765 A1 Dec. 29, 2005

(30) Foreign Application Priority Data

Jun. 29, 2004 (JP) ............... 2004-190974

(51) Int. Cl.
*G01N 27/453* (2006.01)
(52) U.S. Cl. .................. 204/604; 204/601
(58) Field of Classification Search ........ 204/600–605, 204/450–456
See application file for complete search history.

(56) References Cited

U.S. PATENT DOCUMENTS

| | | | |
|---|---|---|---|
| 7,229,540 B2 * | 6/2007 | Okamoto et al. ........... | 204/453 |
| 2006/0113190 A1* | 6/2006 | Kurnik ..................... | 204/453 |
| 2007/0099200 A1* | 5/2007 | Chow et al. ................ | 435/6 |

FOREIGN PATENT DOCUMENTS

| JP | 11-326274 | 11/1999 |
|---|---|---|
| JP | 2002-323477 A | * 11/2002 |

OTHER PUBLICATIONS

JPO computer English language translation of Toru (JP 2002-323477 A) Nov. 8, 2002.*

* cited by examiner

*Primary Examiner*—Alex Noguerola
(74) *Attorney, Agent, or Firm*—Bachman & LaPointe, P.C.

(57) ABSTRACT

An electrophoresis apparatus 1 has an introducing passage 11 for allowing a sample to move from one end of the introducing passage 11 toward the other end thereof, and an analyzing passage 10, formed so as to cross the introducing passage in a cross-portion 8, for allowing a part of the sample in the cross-portion 8 to be separated from the other part of the sample in the introducing passage 11 to move by electrophoresis, wherein the angle between a downstream portion 10a of the analyzing passage 10 from the cross-portion 8 in an electrophoresis direction, and at least one of an upstream portion of the introducing passage 11 from the cross-portion 8 in a sample moving direction, and a downstream portion of the introducing passage 11 from the cross-portion 8 in the sample moving direction, is an acute angle.

14 Claims, 9 Drawing Sheets

ELECTROPHORESIS APPARATUS

BACKGROUND OF THE INVENTION

1. Field of the Invention

The present invention relates to an electrophoresis apparatus used for rapidly and precisely analyzing a sample.

2. Description of the Prior Art

Conventionally, electrophoresis apparatuses are used for analyzing proteins and nucleic acids in organisms, and very small amounts of substances contained in foods and chemicals (see, e.g., Japanese Patent Laid-Open No. 11-326274).

In such an electrophoresis apparatus, as shown in FIGS. 11A through 11C, an introducing passage 111 and analyzing passage 110, which have a very small cross section (e.g., a width of about 100 micrometers×a depth of about tens micrometers), are formed so as to be perpendicular to each other. In the electrophoresis apparatus shown in FIGS. 11A through 11C, an electrophoresis buffer 114 is filled in the introducing passage 111 and analyzing passage 110, and a sample 113 serving as an object to be analyzed is introduced into the introducing passage 111 from one end thereof. Then, as shown in FIG. 12A, the sample 113 is moved by electrophoresis from the one end of the introducing passage 111, in which the electrophoresis buffer 114 is filled, to beyond a cross-portion 108, in which the introducing passage 111 crosses the analyzing passage 110 to be communicated therewith, so that the sample 113 is expanded in the introducing passage 111 (see FIG. 12A). Then, a very small amount of sample 113a positioned in the cross-portion 108 is separated from the other part of the sample 113 in the introducing passage 111 to be moved in the analyzing passage 110 by electrophoresis. Thus, the very small amount of sample 113a containing plural kinds of components is separated into a plurality of bands (a group of materials) in the analyzing passage 110 since they have different electrophoresis speeds (traveling speeds of components due to electrophoresis) in accordance with the difference in molecular weight or the like between the components. Then, if the analyzing passage 110 is irradiated with light from an optical system for analysis, fluorescence is emitted from the fluorescent marker of the sample 113a to be detected by a detecting means (e.g., a light receiving element) to analyze the sample 113a.

However, if the introducing passage 111 and the analyzing passage 110 are formed so as to be substantially perpendicular to each other as the above described conventional apparatus, when a very small amount of sample 113a in the cross-portion 108 is separated to be moved in the analyzing passage 110 by electrophoresis, there are some cases where a part of the sample 113a near the wall surface of the analyzing passage 110 is deformed so as to greatly leave its trails 115, so that adjacent bands overlap with each other to deteriorate performance in the separation of the components (bands) of the sample 113a.

SUMMARY OF THE INVENTION

It is therefore an object of the present invention to eliminate the aforementioned problems and to provide an electrophoresis apparatus capable of decreasing the deformation of a very small amount of sample moving in an analyzing passage by electrophoresis and of improving performance in the separation of components of the sample.

In order to accomplish the aforementioned and other objects, according to one aspect of the present invention, an electrophoresis apparatus comprises: a body member; an introducing passage, formed in the body member, for allowing a sample to move from one end of the introducing passage toward the other end thereof; and an analyzing passage, formed in the body member so as to cross the introducing passage in a cross-portion in which the analyzing passage crosses the introducing passage to be communicated therewith, for allowing a part of the sample in the cross-portion to be separated from the other part of the sample in the introducing passage to move by electrophoresis, wherein the angle between a downstream portion of the analyzing passage from the cross-portion in an electrophoresis direction, in which the part of the sample moves by electrophoresis, and at least one of an upstream portion of the introducing passage from the cross-portion in a sample moving direction, in which the sample moves, and a downstream portion of the introducing passage from the cross-portion in the sample moving direction, is an acute angle.

In this electrophoresis apparatus, the body member may be a plate member. The analyzing passage may be a linear passage, and each of the upstream and downstream portions of the introducing passage may be a linear passage. The body member may have openings which are open to the outside and which are communicated with both ends of each of the introducing passage and the analyzing passage, respectively.

According to another aspect of the present invention, an electrophoresis apparatus comprises: a body member; an introducing passage, formed in the body member, for allowing a sample to move from one end of the introducing passage toward the other end thereof; and an analyzing passage, formed in the body member so as to cross the introducing passage in a cross-portion in which the analyzing passage crosses the introducing passage to be communicated therewith, for allowing apart of the sample in the cross-portion to be separated from the other part of the sample in the introducing passage to move by electrophoresis, wherein corner portions of the cross-portion on the side of an upstream portion of the analyzing passage from the cross-portion in an electrophoresis direction, in which the part of the sample moves by electrophoresis, are chamfered.

In this electrophoresis apparatus, the body member may be a plate member. Each of the introducing passage and the analyzing passage maybe a linear passage, and the analyzing passage may be substantially perpendicular to the introducing passage. In this case, the corner portions may be chamfered so as to have curved surfaces. Alternatively, the corner portions may be chamfered so as to be oblique with respect to the introducing and analyzing passages. The body member has openings which are open to the outside and which are communicated with both ends of each of the introducing passage and the analyzing passage, respectively.

According to the present invention, when a very small amount of part of a sample in the cross-portion is separated from the other part of the sample to be moved in the analyzing passage by electrophoresis, it is difficult for the part of the sample to leave its trails and to be deformed, so that it is possible to improve performance in the separation of components of the sample.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings:

FIG. 1C is a sectional view taken along line IC-IC of FIG. 1A;

FIG. 2B is a side view of the first member, and FIG. 2C is a sectional view taken along line IIC-IIC of FIG. 2A;

DESCRIPTION OF THE PREFERRED EMBODIMENTS

Referring now to the accompanying drawings, the preferred embodiments of an electrophoresis apparatus according to the present invention will be described below in detail.

First Preferred Embodiment

Figure 1A:
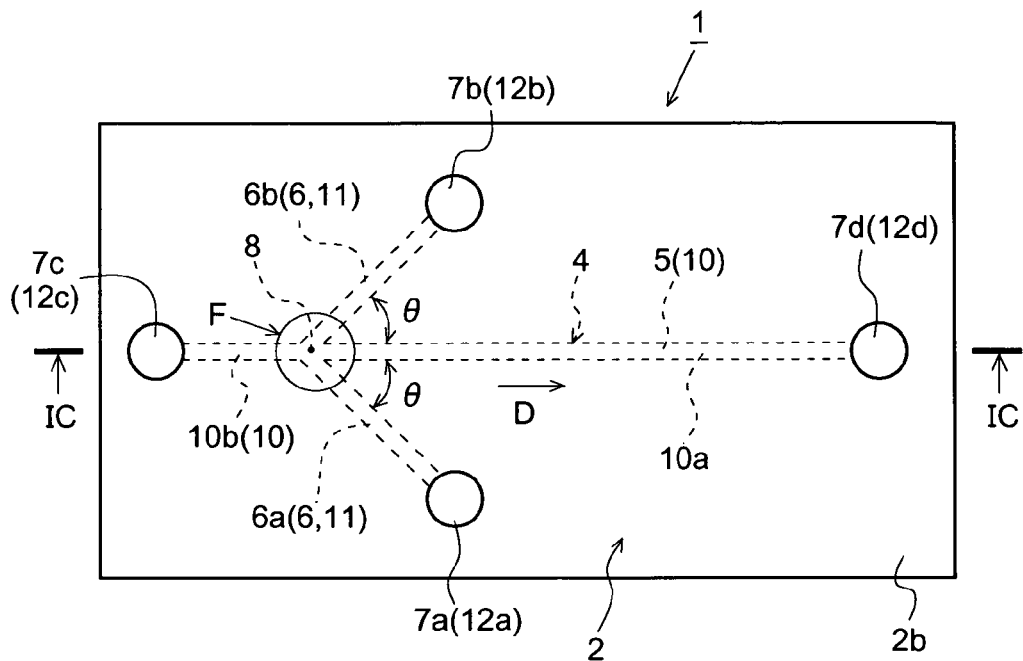
FIGS. 1A through 1C show the first preferred embodiment of an electrophoresis apparatus according to the present invention, FIG. 1A being a plan view of the electrophoresis apparatus, FIG. 1B being a side view of the electrophoresis apparatus.
Figure 1B:
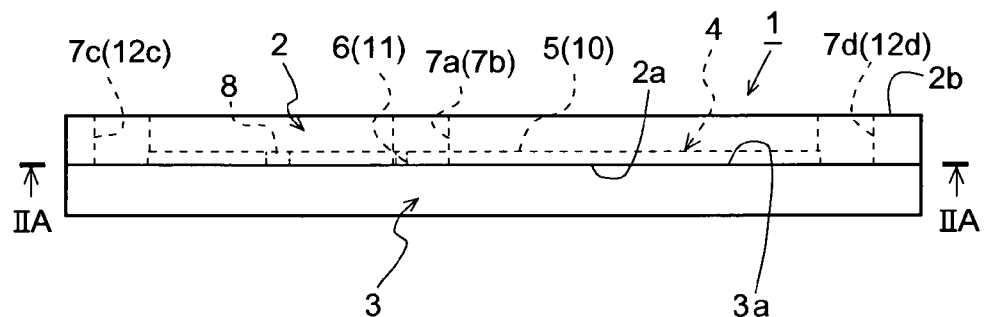
Figure 1C:
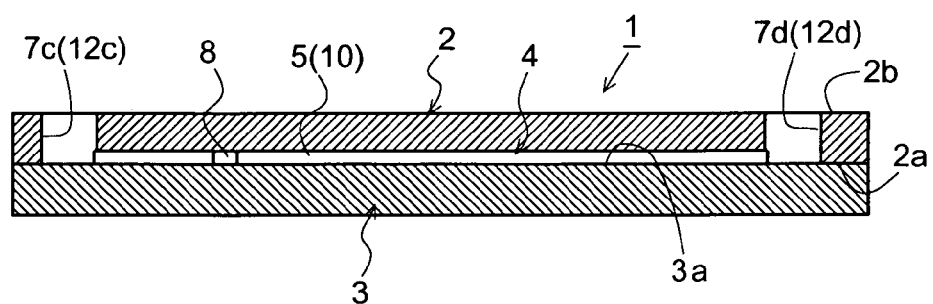

FIGS. 1A through 1C show the first preferred embodiment of an electrophoresis apparatus 1 according to the present invention. As shown in FIGS. 1A through 1C, the electrophoresis apparatus 1 in this preferred embodiment comprises a first member 2, which is a rectangular thin plate, and a second member 3 which is a rectangular thin plate and which is put on the reverse 2a of the first member 2 so as to be aligned therewith. The first member 2 and the second member 3 are fixed to each other while the facing surface of the first member 2 tightly contacts the facing surface of the second member 3. The fixing of the first member 2 to the second member 3 may be carried out by any one of methods for sticking them on each other by utilizing the adhesion of the materials thereof, for fixing them to each other by an adhesive, and for fixing them to each other by means of fixing members such as clips or screws. The best fixing method is suitably chosen in accordance with the materials of the first member 2 and second member 3 and so forth. The materials of the first member 2 and second member 3 are suitably selected from various resin materials, such as polymethyl methacrylate (PMMA), polycarbonate (PC) and ultraviolet curable resins, glasses and ceramics. While the first member 2 and the second member 3 have been thin plates in the embodiment of FIGS. 1A through 1C, the present invention should not be limited thereto. For example, the first member 2 and the second member 3 may be a block-shaped member which has a simple shape of a rectangular parallelepiped or which has a complicated shape obtained by combining a plurality of rectangular parallelepipeds, thin plates and so forth. The facing surfaces 2a and 3a of both members 2 and 3 are preferably flat surfaces having good adhesion.

As shown in FIGS. 1A through 2C, the facing surface 2a of the first member 2 of the electrophoresis apparatus 1 facing the second member 3 has a very small groove 4. The very small groove 4 of the first member 2 comprises a linearly extending analyzing groove 5 and an introducing groove 6 which crosses the analyzing groove 5 to be communicated therewith. At both ends of the analyzing groove 5 and at both ends of the introducing groove 6, through holes 7a through 7d having a planar shape of a circle are formed so as to pass through the first member 2 from the surface 2a to the opposite surface 2b. For example, the analyzing groove 5 and the introducing groove 6 have a width of about 100 micrometers and a depth of about tens micrometers.

The introducing groove 6 crosses the analyzing groove 5 so as to be symmetrical with respect to the center line of the analyzing groove 5 extending in longitudinal directions. The cross angle between the introducing groove 6 and the downstream portion of the analyzing groove 5 from the cross-portion 8 in the electrophoresis direction (traveling direction) of the sample (in a direction shown by arrow D in FIGS. 1A and 2A) is an acute angle. In this preferred embodiment, the introducing groove 6 and the analyzing groove 5 are formed so that the cross angle θ between the introducing groove 6 and the downstream portion of the analyzing groove 5 is 45 degrees.

As shown in FIGS. 1B and 1C, the second member 3 is put on the surface 2a of the first member 2 having the very small groove 4 so as to be aligned with the first member 2. Thus, the opening portions of the analyzing groove 5 and introducing groove 6 of the first member 2, and one end of each of the through holes 7a through 7d of the first member 2 are closed by the second member 3. Then, the analyzing groove 5 forms an analyzing passage 10, the introducing groove 6 forms an introducing passage 11, and the through holes 7a through 7d form reservoirs 12a through 12d.

The second member 3 is a member for closing the opening portions of the very small groove 4 and one end of each of the through holes 7a through 7d of the first member 2 as described above, and serves as a lid member. The surface 3a of the second member 3, which is to be put on the surface 2a of the first member 2 so as to be aligned therewith, is a flat surface which is designed to tightly contact the surface 2a of the first member 2. Thus, the sealing performance of the sample injected into the analyzing passage 10, introducing passage 11 and reservoirs 12a through 12d can be ensured on the facing surfaces of the first member 2 and second member 3, so that it is possible to surely prevent the sample from leaking from the analyzing passage 10, introducing passage 11 and reservoirs 12a through 12d. Furthermore, at least regions of the surface 3a of the second member 3 surrounding the very small groove 4 and through holes 7a through 7d of the first member 2 may be flat so as to tightly contact the surface 2a of the first member 2 so long as it is possible to fulfill the above described function of the lid member.

Figure 3A:
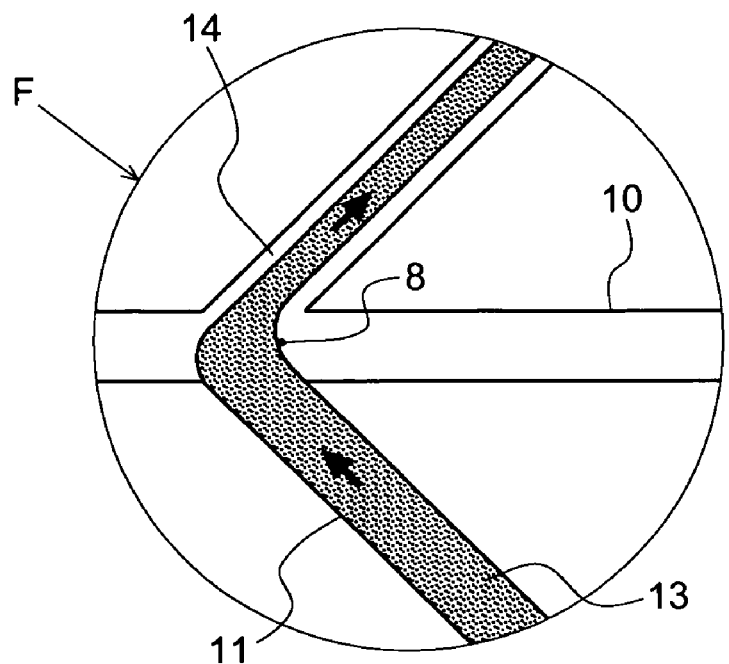
FIGS. 3A and 3B are enlarged illustrations shown by taking a portion F of FIG. 1A, FIG. 3A showing a state that a sample is expanded in an introducing passage, and FIG. 3B showing a state that a part of the sample in a cross-portion is separated into an analyzing passage to be moved therein by electrophoresis.
Figure 3A:

In the electrophoresis apparatus 1 with such a construction, an electrophoresis buffer is injected into each of the reservoirs 12a through 12d to be filled in the introducing passage 11 and analyzing passage 10. Then, a sample to be analyzed is injected into the reservoir (e.g., the reservoir 12a) at one end of the introducing passage 11. Then, for example, if the sample is charged to be negative, the interior of the reservoir 12a at the one end of the introducing passage 11 is grounded, and the interior of each of the reservoirs 12c and 12d at both ends of the analyzing passage 10 is grounded while a voltage (e.g., 100 V) is applied into the reservoir 12b at the other end of the introducing passage 11. As a result, the sample 13 injected into the introducing passage 11 from the reservoir 12a at the one end of the introducing passage 11 is moved by electrophoresis in the introducing passage 11, which is filled with the electrophoresis buffer 14, to pass through the cross-portion 8 to be expanded toward the other end of the introducing passage 11 (see FIG. 3A).

Then, the interior of the reservoir 12c at one end (the upstream end in the electrophoresis direction (in the direction shown by arrow D in FIG. 1A)) of the analyzing passage 10 is grounded, and a voltage (e.g., 150 V) is applied into the reservoir 12d at the other end (the downstream end in the electrophoresis direction) of the analyzing passage 10. In addition, a lower voltage (e.g., 50 V) than the voltage applied to the reservoir 12d is applied into each of the reservoirs 12a and 12b of both ends of the introducing passage 11.

Figure 3B:
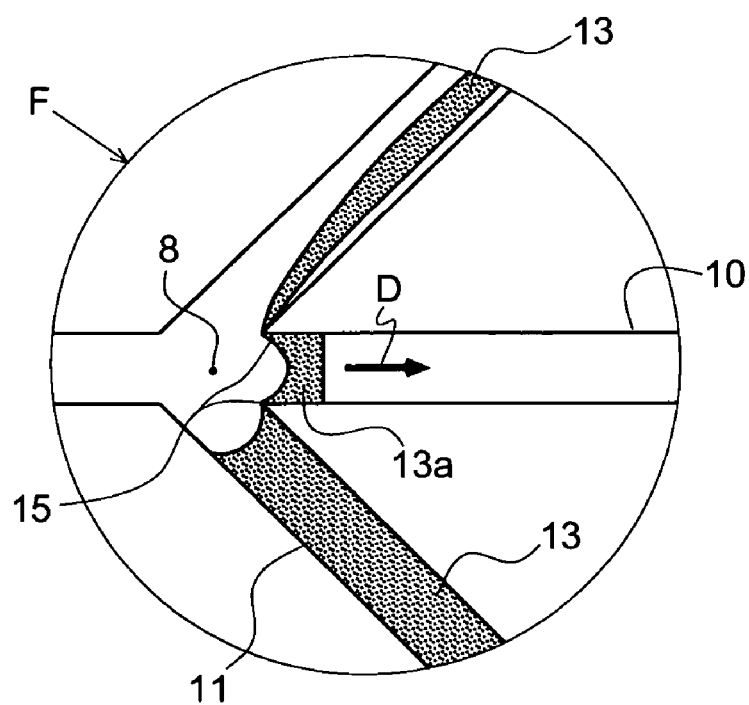

As a result, a very small amount of sample 13a positioned in the cross-portion 8, in which the introducing passage 11 crosses analyzing passage 10, is separated from the other part of the sample 13 in the introducing passage 11 to be moved by electrophoresis in the analyzing passage 10 from the cross-portion 8 toward the other end of the analyzing passage 10 (in a direction shown by arrow D in FIG. 3B).

Figure 11A:
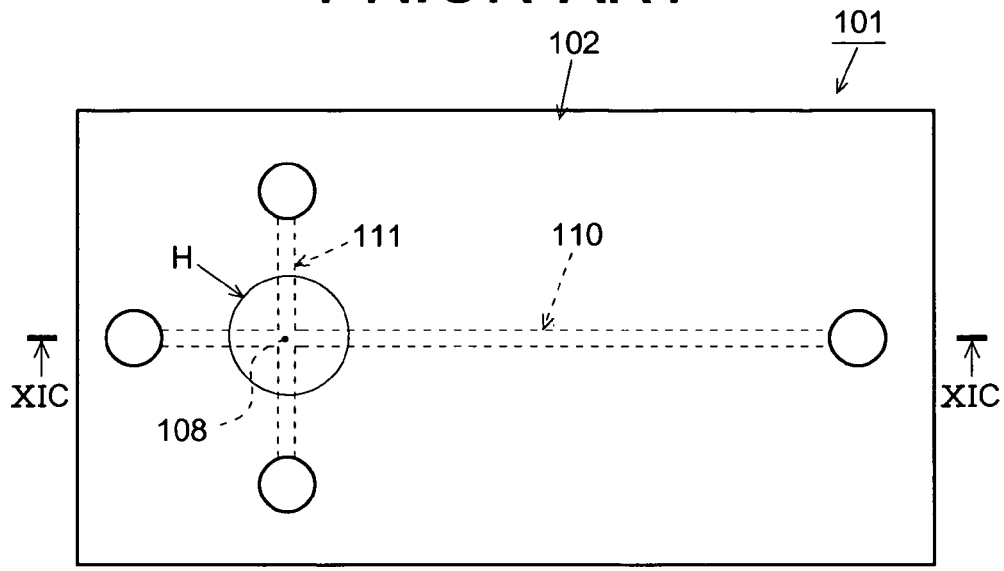
FIGS. 11A through 11C show a conventional electrophoresis apparatus, FIG. 11A being a plan view of the electrophoresis apparatus, FIG. 11B being a side view of the electrophoresis apparatus, and FIG. 11C being a sectional view taken along line XIC-XIC of FIG. 11A.
Figure 12A:
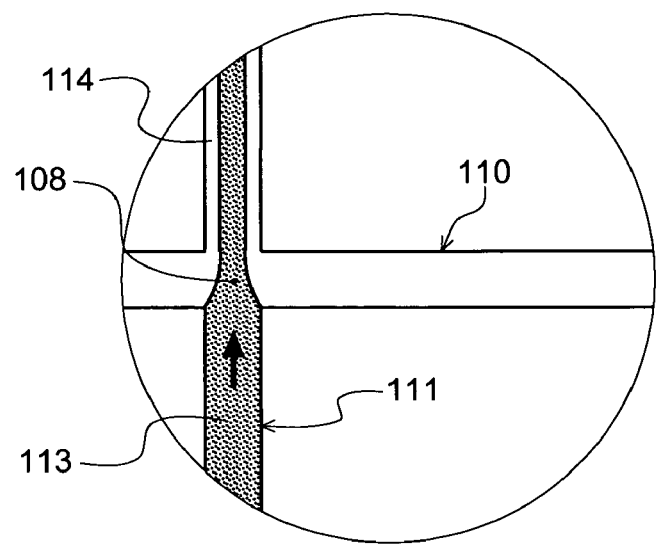
FIGS. 12A and 12B are enlarged illustrations shown by taking a portion H of FIG. 11A, FIG. 12A showing a state that a sample is expanded in an introducing passage, and FIG. 12B showing a state that a part of the sample in a cross-portion is separated into an analyzing passage to be moved therein by electrophoresis.
Figure 12B:
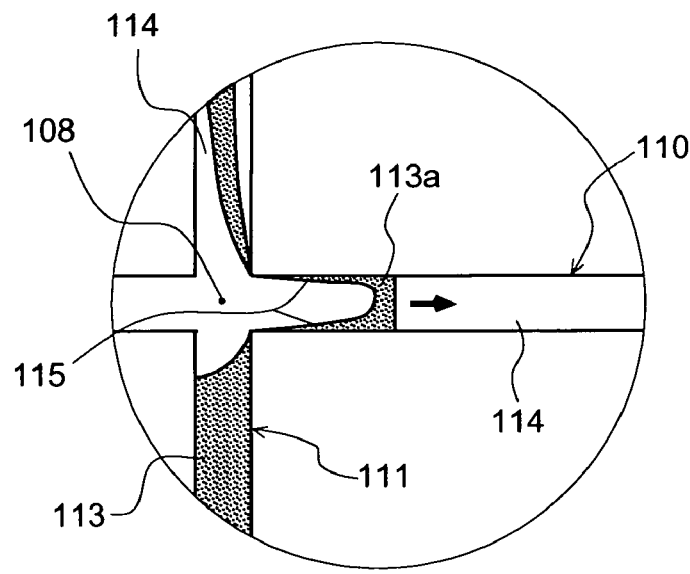

At this time, the very small amount of sample 13a to be separated in the cross-portion 8 is easily separated from the other part of the sample 13 in the introducing passage 11 since the cross angle between the introducing passage 11 and the downstream portion 10a of the analyzing passage 10 in the electrophoresis direction is about 45 degrees which is an acute angle and since the acutely crossing portion is sharp. As a result, the amount of the trail 15 of the very small amount of sample 13a, which travels in the analyzing passage 10 by electrophoresis, is small in the analyzing passage 10 as shown in FIG. 3B. On the other hand, in the conventional electrophoresis apparatus 101 wherein the introducing passage 111 crosses the analyzing passage 110 so as to be substantially perpendicular thereto as shown in FIG. 11A, a very small amount of sample 113a in the cross-portion 108, in which the introducing passage 111 crosses the analyzing passage 110, greatly leaves its trail 115 when the sample 113a moves in the analyzing passage 110 by electrophoresis (see FIG. 12B). As can be seen from the comparison of the electrophoresis apparatus 1 in this preferred embodiment with the conventional electrophoresis apparatus 101, the shapes of the very small amount of samples 13a and 113a traveling in the analyzing passages 10 and 110 by electrophoresis are greatly different from each other (see FIGS. 3B and 12B).

Figure 8A:
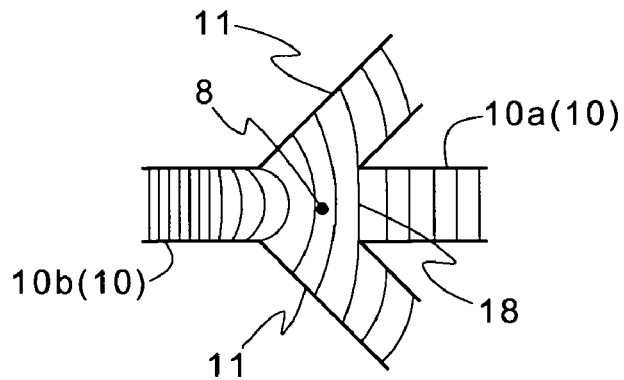
FIGS. 8A and 8B are illustrations showing equipotential surfaces caused when a sample is moved in an analyzing passage by electrophoresis, FIG. 8A being an illustration showing equipotential surfaces when the first member in the first preferred embodiment shown in FIGS. 1A through 3B is used, and FIG. 8B being an illustration showing equipotential surfaces when the first member of FIG. 6 is used.

In the electrophoresis apparatus 1 in this preferred embodiment, the very small amount of sample 13a charged to be negative is moved by electrophoresis in the analyzing passage 10. Therefore, for example, if a voltage of 50 V is applied to both ends of the introducing passage 11 and if the end portion of the upstream portion 10b of the analyzing passage 10 in the electrophoresis direction is grounded while a voltage of 150 V is applied to the end portion of the downstream portion 10a of the analyzing passage 10 in the electrophoresis direction (see FIG. 1A), equipotential surfaces 18 in an end portion (the end portion on the side of the cross-portion 8) of the downstream portion 10a of the analyzing passage 10 in the electrophoresis direction are substantially perpendicular to the analyzing passage 10 as shown in FIG. 8A, so that the sample 13a in the cross-portion 8 is separated to be introduced into the analyzing passage 10 in such a state that it is difficult to leave its trail (see FIG. 3B).

Therefore, the above described function of such a shape that the analyzing passage 10 crosses the introducing passage 11 at an acute angle is combined with such a function that the equipotential surfaces 18 are substantially perpendicular to the downstream portion 10a of the analyzing passage 10 in the electrophoresis direction, to allow the very small amount of sample 13a positioned in the cross-portion 8 to be surely separated from the other part of the sample 13 in the introducing passage 11 in such a state that it is difficult to leave its trail 15 (see FIG. 3B). On the other hand, in the case of the conventional electrophoresis apparatus wherein the analyzing passage 110 is perpendicular to the introducing passage 111, equipotential surfaces 118 in an end portion (in the end portion on the side of the cross-portion 108) of the downstream portion 110a of the analyzing passage 110 in the electrophoresis direction are greatly curved, so that the sample 113 in the cross-portion 108 is separated to be introduced into the analyzing passage 110 in such a state that it is easy to leave its trail 115 (see FIG. 12B).

Thus, the very small amount of sample 13a separated in the cross-portion 8 to travel in the analyzing passage 10 by electrophoresis has different electrophoresis speeds (traveling speeds of components due to electrophoresis) in accordance with the difference in molecular weight or the like between the components, so that the components are separated from each other to form a plurality of bands. Since the amount of the trail 15 of the sample 13a is so small as to improve performance in the separation of the bands, it is difficult for the trail of the leading band of adjacent two of the bands in the analyzing passage 10 to overlap with the trailing band of the adjacent two of the bands, so that it is possible to more rapidly (high throughput) and precisely analyze the sample than the conventional electrophoresis apparatus.

Figures 10A, 10B:
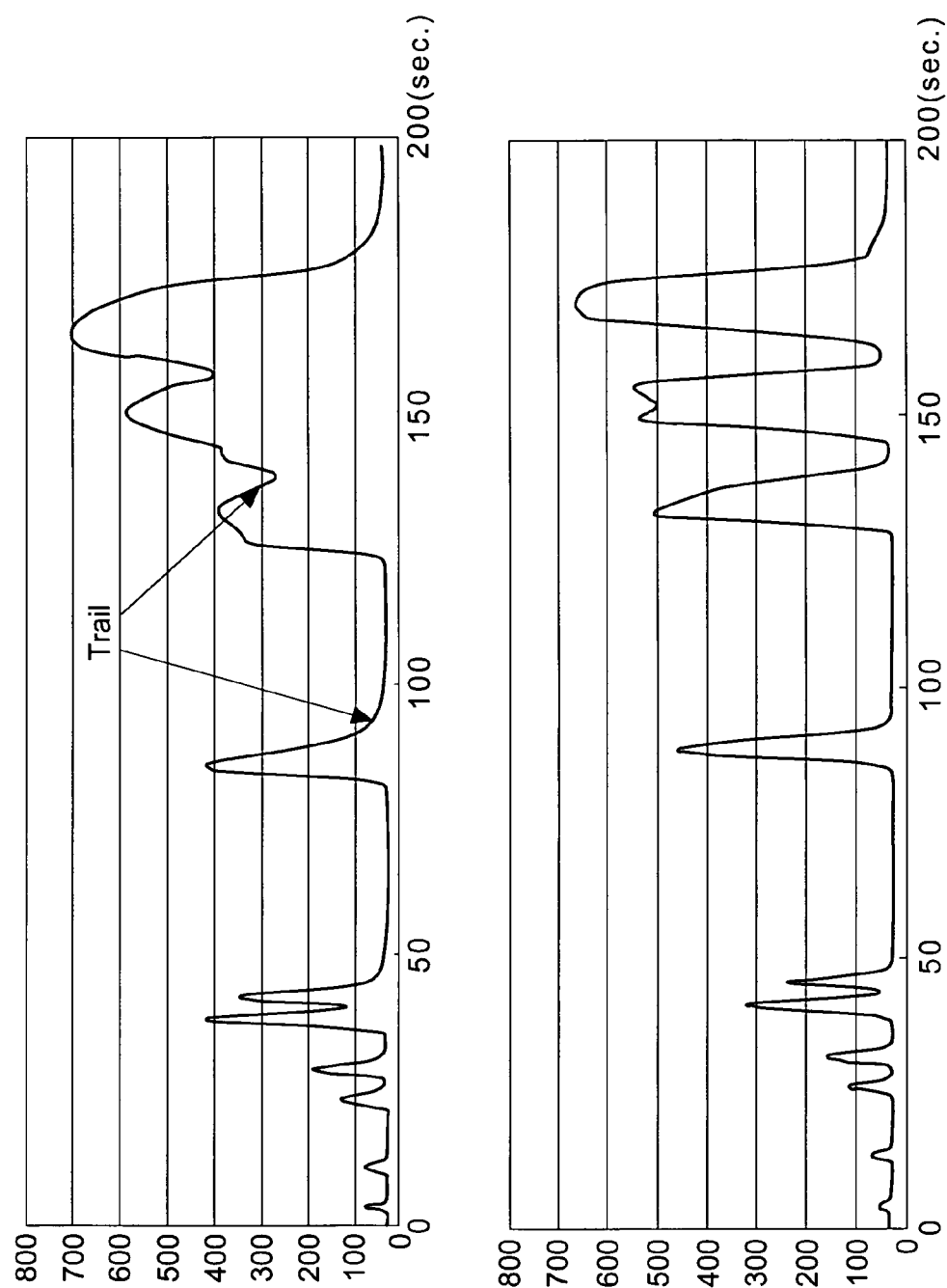
FIGS. 10A and 10B are graphs showing the results of analysis of samples, FIG. 10A showing the results of analysis of a sample in a conventional electrophoresis apparatus, and FIG. 10B showing the results of analysis of a sample in the first preferred embodiment of an electrophoresis apparatus according to the present invention.
Figure 11B:
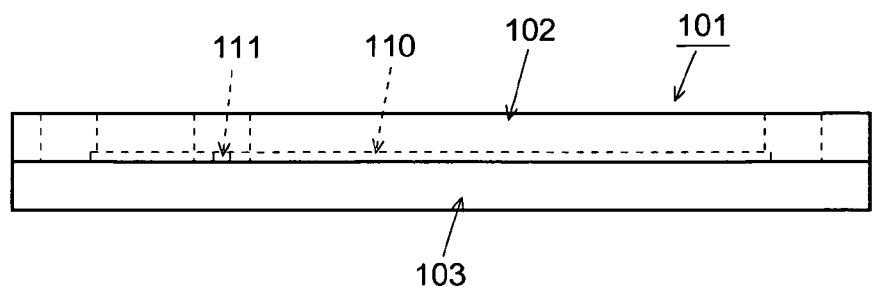
Figure 11C:
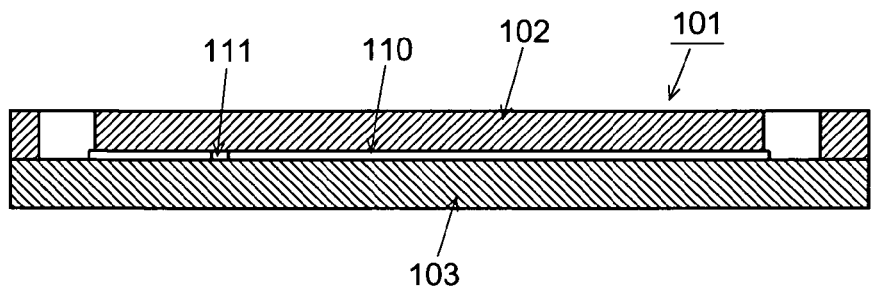

FIGS. 10A and 10B show the results of such analysis of samples. FIG. 10A show the results of analysis of a sample when the conventional electrophoresis apparatus shown in FIGS. 11A through 11C is used, and FIG. 10B shows the result of analysis of a sample when the electrophoresis apparatus 1 in this preferred embodiment shown in FIGS. 1A through 1C is used. Furthermore, in FIGS. 10A and 10B, the axis of abscissas denotes time (seconds) and the axis of ordinates denotes the intensity of fluorescence (relative values to an arbitrary reference value when the reference value is set to be 100).

As shown in FIGS. 10A and 10B, in the conventional electrophoresis apparatus 101, the sample is easy to leave its trail in the analyzing passage 110, so that adjacent bands overlap with each other so as not to be clearly separated and independent from each other (see FIG. 10A). On the other hand, in the electrophoresis apparatus 1 in this preferred embodiment, it is difficult for the sample to leave its trail in the analyzing passage 10, so that adjacent bands do not overlap with each other to be clearly separated and independent from each other as shown in FIG. 10B. Thus, the electrophoresis apparatus 1 in this preferred embodiment can more precisely analyze the sample than the conventional electrophoresis apparatus 101.

Furthermore, the electrophoresis apparatus 1 in this preferred embodiment can be applied to a sample analysis wherein light is emitted from a light emitting device of a detecting means to a sample reaching a detected position in the analyzing passage 10 and wherein fluorescence emitted from a fluorescent marker of the sample is received and detected by a light receiving device of the detecting means, as well as to other sample analyses (e.g., sample analyses for magnetically detecting a sample, analyses based on absorption of light such as ultraviolet, and electrochemical analyses).

Figure 2A:
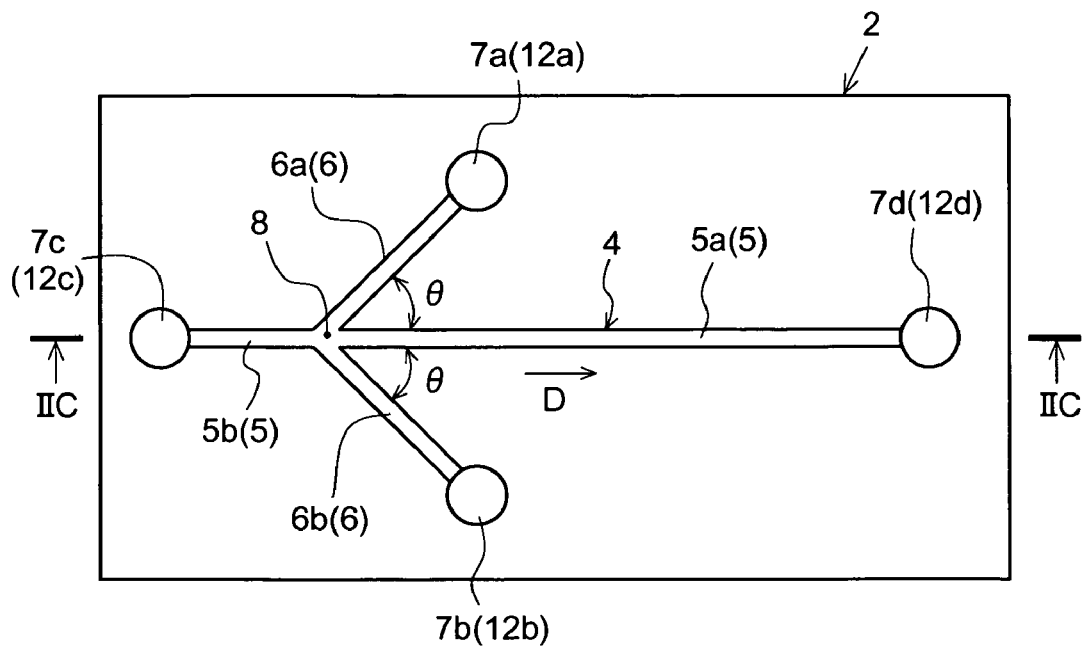
FIGS. 2A through 2C show a first member forming the electrophoresis apparatus of FIGS. 1A through 1C, FIG. 2A being a plan view of a facing surface of the first member (a surface obtained by separating a second member from the first member so as to be taken along line IIA-IIA of FIG. 1B)
Figure 2B:
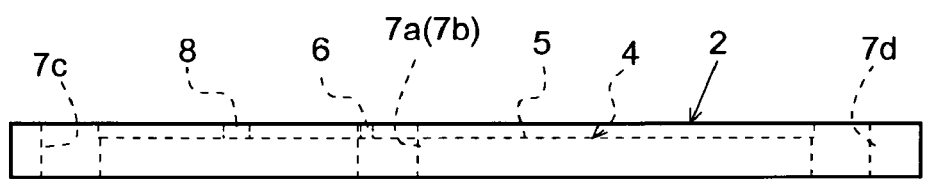
Figure 2C:
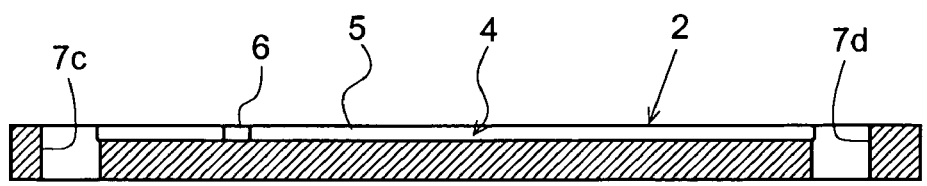
Figure 4:
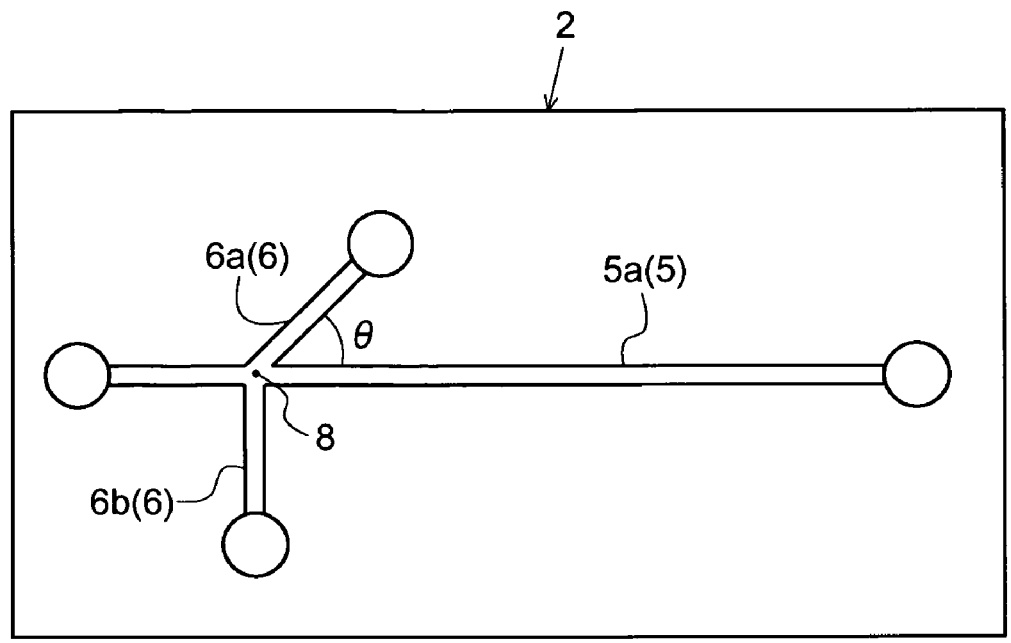
FIG. 4 is a plan view showing a first modified example of the first member.
Figure 5:
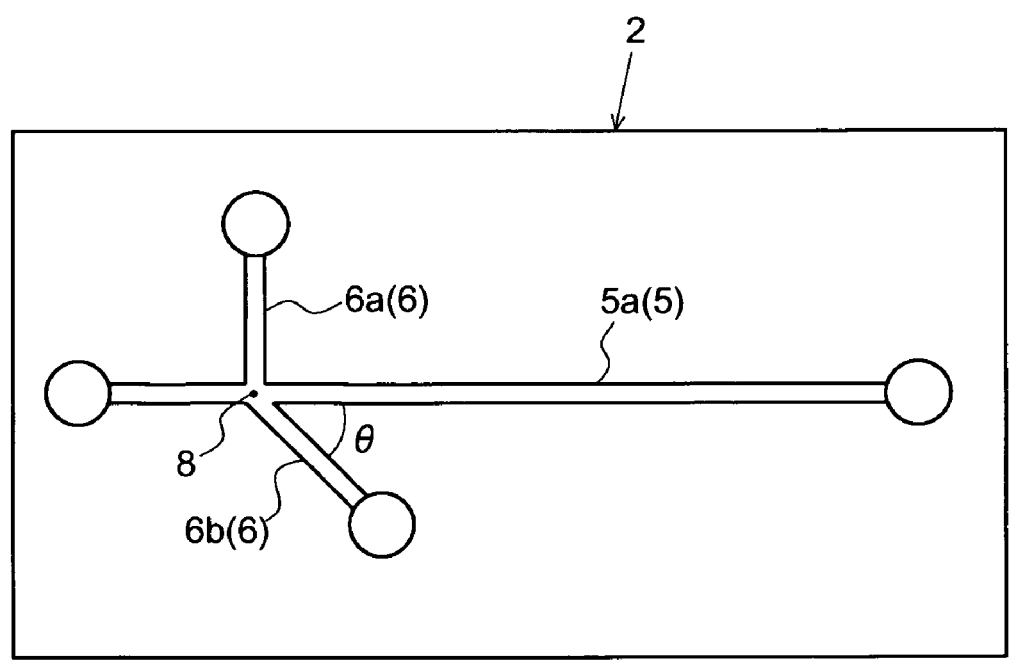
FIG. 5 is a plan view showing a second modified example of the first member.

As shown in FIG. 2A, in the first member 2 in this preferred embodiment, the upstream portion 6a and downstream portion 6b of the introducing groove 6 are formed on both sides of the linear analyzing groove 5 so as to be symmetrical with respect to the analyzing groove 5, and the cross angles between the introducing grooves 6a, 6b and the downstream portion 5a of the analyzing groove 5 from the cross-portion 8 in the electrophoresis direction are an acute angle θ. However, the present invention should not be limited thereto. For example, as shown in FIGS. 4 and 5, the cross angle between only one of the upstream portion 6a and downstream portion 6b of the introducing groove 6 and the downstream portion 5a of the analyzing groove 5 in the electrophoresis direction may be an acute angle θ. Also with such constructions, it is possible to substantially obtain the same advantageous effects as those in the electrophoresis apparatus 1 shown in FIGS. 1A through 3B, and the very small amount of sample 13a positioned in the cross-portion 8 is separated to move in the analyzing passage 10 in such a state that it is difficult to leave its trail 15 in comparison with the conventional electrophoresis apparatus shown in FIGS. 11A through 12B (see FIG. 3B).

The first member 2 and second member 3 in this preferred embodiment are formed of a material having a good light permeability. However, the present invention should not be limited thereto. The first member 2 and the second member 3 may be formed of a shading material in accordance with a sample analyzing method. Alternatively, one of the members 2 and 3 may be formed of a material having an excellent light permeability, and the other member may be formed of a shading material. Moreover, only a part of the members 2 and 3 may be formed of a material having an excellent light permeability.

While the cross angle θ between the introducing groove 6 and the analyzing groove 5 has been 45 degrees, the present invention should not be limited thereto, but the optimum angle (90°>θ) may be suitably chosen in accordance with characteristics of samples and so forth.

Second Preferred Embodiment

Figure 6:
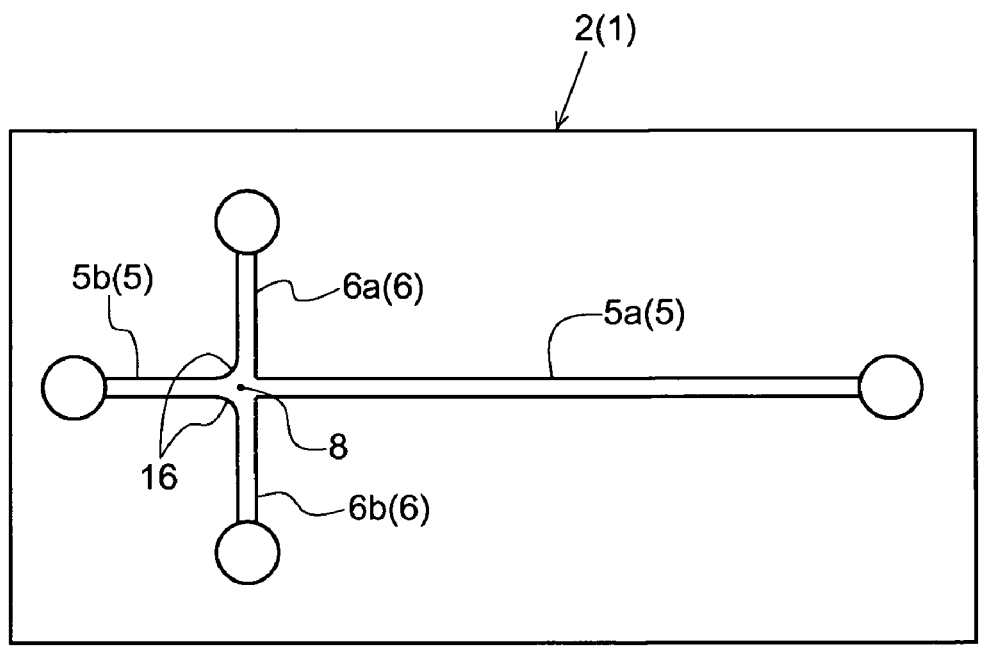
FIG. 6 is a plan view showing a first member of the second preferred embodiment of an electrophoresis apparatus according to the present invention.
Figure 7:
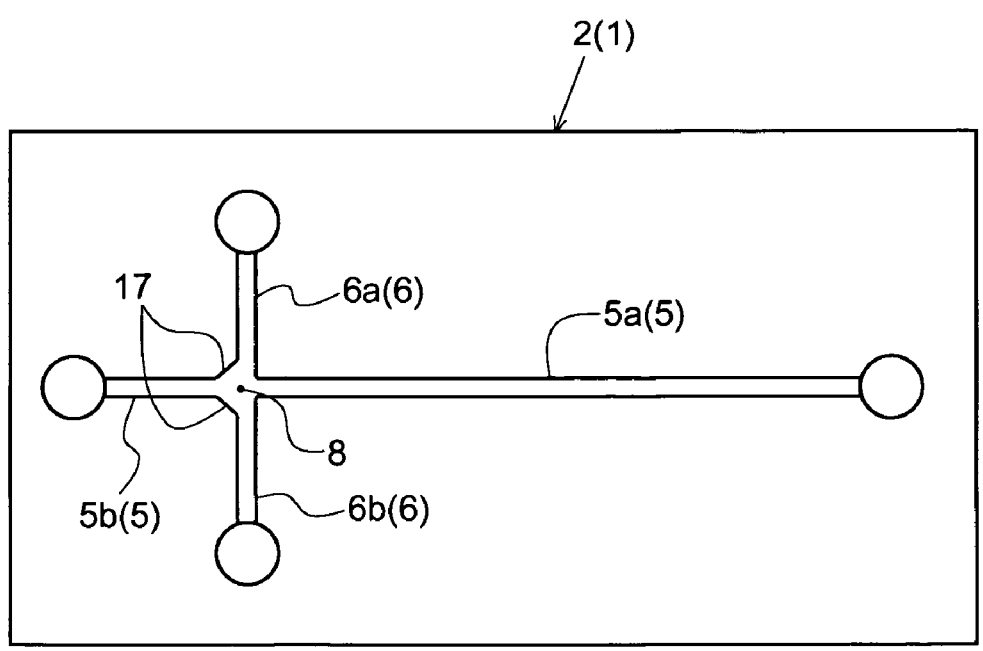
FIG. 7 is a plan view showing a modified example of the first member of FIG. 6.

FIGS. 6 and 7 show a first member 2 in the second preferred embodiment of an electrophoresis apparatus 1 according to the present invention. As shown in these figures, the first member 2 in this preferred embodiment has a linear introducing groove 6 and a linear analyzing groove 5 which crosses the introducing groove 6 so as to be substantially perpendicular thereto. In the first member 2, the corner portions of the cross-portion 8, in which the introducing groove 6 crosses the analyzing groove 5, on the side of the upstream portion 5b of the analyzing groove 5 from the cross-portion 8 in the electrophoresis direction are chamfered so as to have curved surfaces (R-chamfered surfaces 16) (see FIG. 6), or linearly and obliquely chamfered so as to have oblique surfaces (C-chamfered surfaces 17) (see FIG. 7). Furthermore, the R-chamfer dimension and C-chamfer dimension on the corner portions of the cross-portion 8 of the first member 2 are about 100 μm which is about twenty times as large as the dimension (5 μm) of sagging (rounding on the corner portions) caused by molding. However, the R-chamfer dimension and C-chamfer dimension should not be limited to the above described dimension, and the optimum R-chamfer and C-chamfer dimensions may be suitably determined in accordance with the shape and dimension of the analyzing groove 5 and introducing groove 6.

Figure 8B:
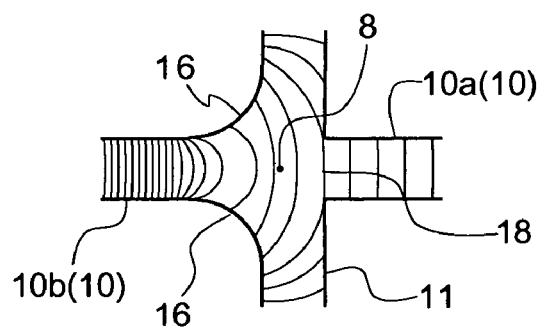
Figure 9:
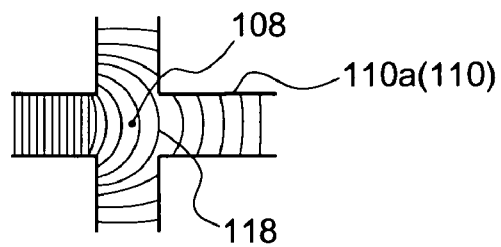
FIG. 9 is an illustration showing equipotential surfaces caused when a sample in a cross-portion is moved by electrophoresis in an analyzing passage of a conventional electrophoresis apparatus.

According to this preferred embodiment with such constructions, the second member 3 is put on the first member 2 of FIG. 6 or 7 so as to be aligned therewith to form the electrophoresis apparatus 1. In order to move a very small amount of sample 13a, which is charged to be negative, by electrophoresis in the analyzing passage 10, for example, if a voltage of 50 V is applied to both ends of the introducing passage 11 and if the end of the upstream portion 10b of the analyzing passage 10 in the electrophoresis direction is grounded while a voltage of 150 V is applied to the end of the downstream portion 10a of the analyzing passage 10 in the electrophoresis direction (see FIG. 1A), the equipotential surfaces 18 in an end portion (on the end portion on the side of the cross-portion 8) of the downstream portion 10a of the analyzing passage 10 in the electrophoresis direction are substantially perpendicular to the analyzing passage 10 as shown in FIG. 8B, so that the sample 13a in the cross-portion 8 is separated to be introduced into the analyzing passage 10 in such a state that it is difficult to leave its trail 15 (see FIG. 3B). On the other hand, if the R-chamfering or C-chamfering of the corner portions of the cross-portion 108 is not carried out, the equipotential surfaces 118 in an end portion (the end portion on the side of the cross-portion 108) of the downstream portion 110a of the analyzing passage 110 in the electrophoresis direction are greatly curved as shown in FIG. 9, so that the sample 113 in the cross-portion 108 is separated to be introduced into the analyzing passage 110 in such a state that it is easy to leave its trail 115 (see FIG. 12B).

In the electrophoresis apparatus 1 with such constructions, the very small amount of sample 13a separated in the cross-portion 8 to travel in the analyzing passage 10 by electrophoresis has different electrophoresis speeds (traveling speeds of components due to electrophoresis) in accordance with the difference in molecular weight or the like between the components, so that the components are separated from each other to form a plurality of bands. Since the amount of the trail 15 of the sample 13a is so small as to improve performance in the separation of the bands, it is difficult for the trail of the leading band of adjacent two of the bands in the analyzing passage 10 to overlap with the trailing band of the adjacent two of the bands, so that it is possible to more rapidly (high throughput) and precisely analyze the sample than the conventional electrophoresis apparatus.

While the introducing groove 6 and the analyzing groove 5 have been formed in the first member 2 in the above described preferred embodiments, the present invention should not be limited thereto. The introducing groove 6 and the analyzing groove 5 may be formed in the second member 3, and only the through holes 7a through 7d may be formed in the first member 2.

In the electrophoresis apparatus 1 in the above described first preferred embodiment, the corner portions of the cross-portion 8, in which the introducing groove 6 crosses the analyzing groove 5, on the side of the upstream portion 5b of the analyzing groove 5 of the first member 2 from the cross-portion 8 in the electrophoresis direction maybe chamfered so as to have curved surfaces (see FIG. 6), or linearly and obliquely chamfered so as to have oblique surfaces (see FIG. 7).

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. An electrophoresis apparatus comprising:
    a body member;
    an introducing passage, formed in said body member, for allowing a sample to move from one end of the introducing passage toward the other end thereof; and
    an analyzing passage, formed in said body member so as to cross said introducing passage in a cross-portion in which the analyzing passage crosses said introducing passage to be communicated therewith, for allowing a part of said sample in said cross-portion to be separated from the other part of said sample in said introducing passage to move by electrophoresis,
    wherein each of said introducing passage and said analyzing passage is a linear passage, and said analyzing passage is substantially perpendicular to said introducing passage, and
    wherein corner portions of said cross-portion on the side of an upstream portion of said analyzing passage from said cross-portion in an electrophoresis direction, in which said part of said sample moves by electrophoresis, are chamfered so as to have curved surfaces.

2. An electrophoresis apparatus as set forth in claim 1, wherein said body member is a plate member.

3. An electrophoresis apparatus as set forth in claim 1, wherein said body member has openings which are open to the outside and which are communicated with both ends of each of said introducing passage and said analyzing passage, respectively.

4. An electrophoresis apparatus comprising:
    a body member;
    an introducing passage, formed in said body member, for allowing a sample to move from one end of the introducing passage toward the other end thereof; and
    an analyzing passage, formed in said body member so as to cross said introducing passage in a cross-portion in which the analyzing passage crosses said introducing passage to be communicated therewith, for allowing a part of said sample in said cross-portion to be separated from the other part of said sample in said introducing passage to move by electrophoresis,
    wherein each of said introducing passage and said analyzing passage is a linear passage, and said analyzing passage is substantially perpendicular to said introducing passage, and
    wherein corner portions of said cross-portion on the side of an up stream portion of said analyzing passage from said cross-portion in an electrophoresis direction, in which said part of said sample moves by electrophoresis, are chamfered so as to be oblique with respect to said introducing and analyzing passages.

5. An electrophoresis apparatus as set forth in claim 4, wherein said body member is a plate member.

6. An electrophoresis apparatus as set forth in claim 4, wherein said body member has openings which are open to the outside and which are communicated with both ends of each of said introducing passage and said analyzing passage, respectively.

7. An electrophoresis apparatus comprising:
    a body member; and
    a pair of passages formed in said body member, said pair of passages consisting of an introducing passage and an analyzing passage,
    said introducing passage allowing a sample to move from one end of the introducing passage toward the other end thereof, and said analyzing passage crossing said introducing passage in a cross-portion, in which the analyzing passage crosses said introducing passage to be communicated therewith, for allowing a part of said sample in said cross-portion to be separated from the other part of said sample in said introducing passage to move by electrophoresis,
    wherein an angle between a downstream portion of said analyzing passage from said cross-portion in an electrophoresis direction, in which said part of said sample moves by electrophoresis, and at least one of an upstream portion of said introducing passage from said cross-portion in a sample moving direction, in which said sample moves, and a downstream portion of said introducing passage from said cross-portion in said sample moving direction, is an acute angle.

8. An electrophoresis apparatus as set forth in claim 7, wherein said body member is a plate member.

9. An electrophoresis apparatus as set forth in claim 7, wherein said analyzing passage is a linear passage, and each of said upstream and downstream portions of said introducing passage is a linear passage.

10. An electrophoresis apparatus as set forth in claim 7, wherein said body member has openings which are open to the outside and which are communicated with both ends of each of said introducing passage and said analyzing passage, respectively.

11. An electrophoresis apparatus comprising:
a body member;
an introducing passage, formed in said body member, for allowing a sample to move from one end of the introducing passage toward the other end thereof; and
an analyzing passage, formed in said body member so as to cross said introducing passage in a cross-portion in which the analyzing passage crosses said introducing passage to be communicated therewith, for allowing a part of said sample in said cross-portion to be separated from the other part of said sample in said introducing passage to move by electrophoresis,
wherein corner portions of said cross-portion on the side of an upstream portion of said analyzing passage from said cross-portion in an electrophoresis direction, in which said part of said sample moves by electrophoresis, are chamfered so as to widen said cross-portion.

12. An electrophoresis apparatus as set forth in claim 11, wherein said body member is a plate member.

13. An electrophoresis apparatus as set forth in claim 11, wherein each of said introducing passage and said analyzing passage is a linear passage, and said analyzing passage is substantially perpendicular to said introducing passage.

14. An electrophoresis apparatus as set forth in claim 11, wherein said body member has openings which are open to the outside and which are communicated with both ends of each of said introducing passage and said analyzing passage, respectively.

* * * * *